(12) United States Patent
Thomas et al.

(10) Patent No.: US 8,381,743 B1
(45) Date of Patent: Feb. 26, 2013

(54) COMBINED TOOTHPASTE CONTAINER CAP DENTAL FLOSS DISPENSER

(76) Inventors: Lisa Thomas, Hudson, OH (US);
Robert L. Anderson, Durham, NC (US);
Bradley P. Griffin, Greenville, NC (US)

(*) Notice: Subject to any disclaimer, the term of this patent is extended or adjusted under 35 U.S.C. 154(b) by 0 days.

(21) Appl. No.: 13/539,560

(22) Filed: Jul. 2, 2012

Related U.S. Application Data

(60) Provisional application No. 61/594,485, filed on Feb. 3, 2012.

(51) Int. Cl.
*A61C 15/00* (2006.01)
(52) U.S. Cl. .......................................................... 132/325
(58) Field of Classification Search ................... 132/324, 132/325, 329
See application file for complete search history.

(56) References Cited

U.S. PATENT DOCUMENTS

| | | | | |
|---|---|---|---|---|
| 1,733,114 A | * | 10/1929 | Brennan | 132/314 |
| 5,732,722 A | * | 3/1998 | Mortvedt | 132/325 |
| 7,243,663 B1 | * | 7/2007 | Einstein et al. | 132/314 |

* cited by examiner

*Primary Examiner* — Todd E. Manahan
*Assistant Examiner* — Brianne Kalach
(74) *Attorney, Agent, or Firm* — James C. Scott; Roetzel & Andress

(57) ABSTRACT

The combined toothpaste container cap and dental floss dispenser of the present disclosure and related inventions includes a cap structure configured to fit with a toothpaste dispenser in the form of a tube, a floss container and an access panel. The floss container is configured to fit within the cap body and has a floss containment cavity in which a supply of dental floss is stored. A floss lead opening is located on the floss container through which the dental floss is accessed. An access panel is attached to the floss container which covers the floss lead opening.

8 Claims, 6 Drawing Sheets

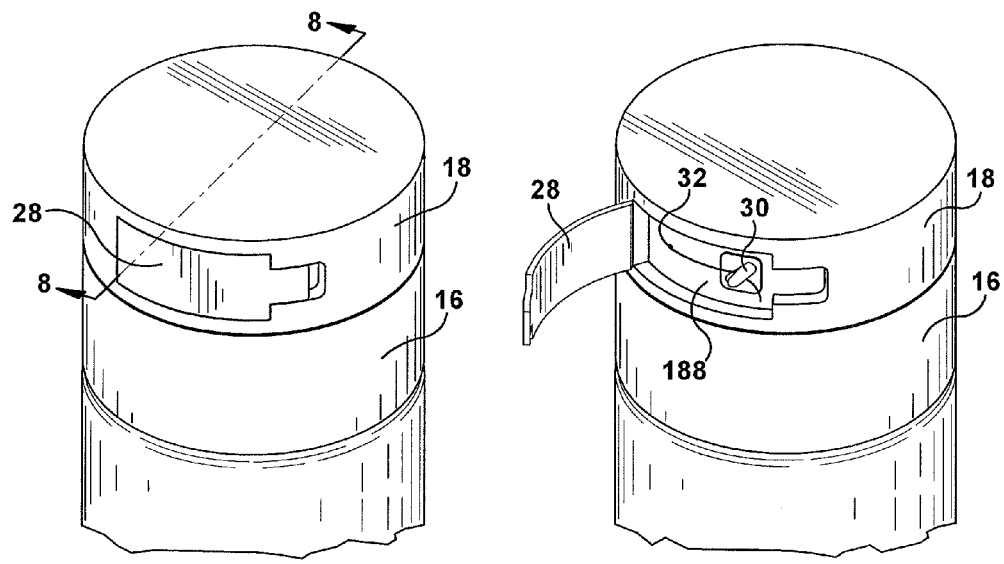
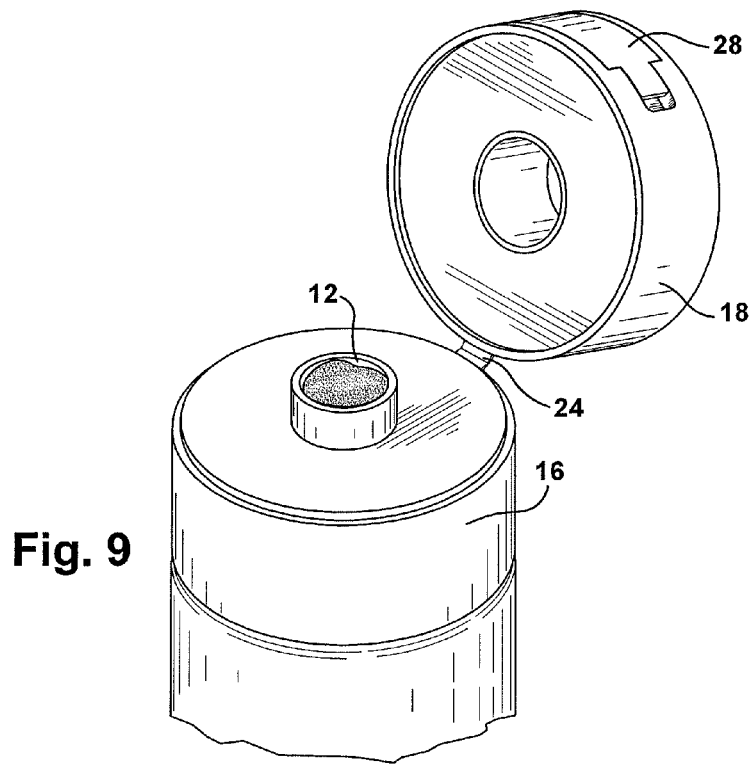
Fig. 7   Fig. 8
Fig. 9

US 8,381,743 B1

COMBINED TOOTHPASTE CONTAINER CAP DENTAL FLOSS DISPENSER

RELATED APPLICATIONS

This application claims priority to U.S. Provisional Patent Application No. 61/594,485, filed on Feb. 3, 2012, a copy of which is incorporated herein by reference in its entirety.

FIELD OF THE INVENTION

The present disclosure and related inventions is in the general field of dental hygiene products and devices, and more particularly in the field of toothpaste and dental floss containers and dispensers.

BACKGROUND OF THE INVENTION

Caps and lids for toothpaste containers and dispensers, such as toothpaste tubes, have been modified to hold a small supply of dental floss, for example on a spool within the cap body, as disclosed for example in U.S. Pat. Nos. 5,732,722 and 7,243,663. These patents disclose particular configurations of such caps including the shape of the cap body and orientation of the floss spool within the cap body, access to the floss through a wall of the cap body, and means for cutting a segment of floss pulled from the spool. These designs are unique, complex and generally configured to fit with existing toothpaste dispensers as aftermarket accessory products. U.S. Pat. No. 5,732,722 also discloses an aftermarket toothpaste container cap with a supply of floss designed to fit on a threaded dispensing port of a toothpaste tube container. The floss container has a spindle-mounted spool on which dental floss is wound for exit through a side opening in the cap body, and a containment plate which is required to retain the floss spool within the cap body. The containment plate adds to the complexity and cost of the assembly and the disclosed openings in the containment plate do not keep the floss sealed and sanitary in the cap. The spool/spindle configuration has limited floss capacity and is restricted to lateral dispensing through the side wall of the cap.

The prior art does not provide a toothpaste container with a combined toothpaste container cap and dental floss dispenser as a fully integrated design and assembly as original manufacturer packaging that contains and dispenses both toothpaste and a large supply of floss in a sterile enclosure which is easily operated and which is economical and efficient to manufacture and assemble.

SUMMARY OF THE INVENTION

The combined toothpaste container cap and dental floss dispenser of the present disclosure and related inventions includes a cap structure configured to fit with a toothpaste dispenser in the form of a tube, a floss container and an access panel. The floss container is configured to fit within the cap body and has a floss containment cavity in which a supply of dental floss is stored. A floss lead opening is located on the floss container through which the dental floss is accessed, dispensed and cut. An access panel is attached to the floss container which covers the floss lead opening and a floss cutter.

In accordance with one aspect of the present disclosure and related inventions, there is provided a combined toothpaste container cap and dental floss dispenser which includes a cap body configured to fit with a toothpaste container; a floss container body configured to fit with the cap body, the floss container body having a floss containment cavity containing a stationary floss cartridge with a supply of dental floss, and a floss lead opening through the floss container body.

In accordance with another aspect of the present disclosure and related inventions, there is provided a combined toothpaste container cap and dental floss dispenser which includes: a toothpaste container tube having a generally cylindrical dispensing port; a cap body configured to fit over a portion of the toothpaste container tube, the cap body having an internal structure which is configured to fit around the dispensing port; a floss container body hingedly attached to the cap body, the floss container body having a floss containment cavity located therein which is configured to hold a continuous strand of dental floss, a floss cartridge with which the continuous strand of floss is engaged, the floss cartridge fixedly engaged with the floss container body, a floss lead opening through which the continuous strand of dental floss is accessed, and an access panel hingedly attached to the floss container body.

These and other aspects of the present disclosure and related inventions are further described herein with reference to the accompanying drawings.

DESCRIPTION OF THE DRAWINGS

FIGS. 7 and 8 are perspective views of an alternate embodiment of a combined toothpaste container cap dental floss dispenser of the disclosure;

FIG. 9 is an alternate perspective view of the combined toothpaste container cap dental floss dispenser of FIGS. 7 and 8.

DETAILED DESCRIPTION OF PREFERRED AND ALTERNATE EMBODIMENTS

The present disclosure and related inventions include, in representative embodiments, various embodiments of combined toothpaste container caps and dental floss dispensers, generally indicated at 100, in combination with toothpaste containers, packages or dispensers such as tube-type or any other type of containment configuration for toothpaste (referred to herein generally and collectively as "containers" or "toothpaste containers"). As depicted by the accompanying drawings, FIGS. 1 through 8, the combined toothpaste container caps and dental floss dispensers 100 are generally configured to fit with any type of toothpaste container, generally indicated at 10, such as, although not limited to, a tube configuration, and in particular any type of container or dispenser which has a dispensing port or outlet.

Figure 3:
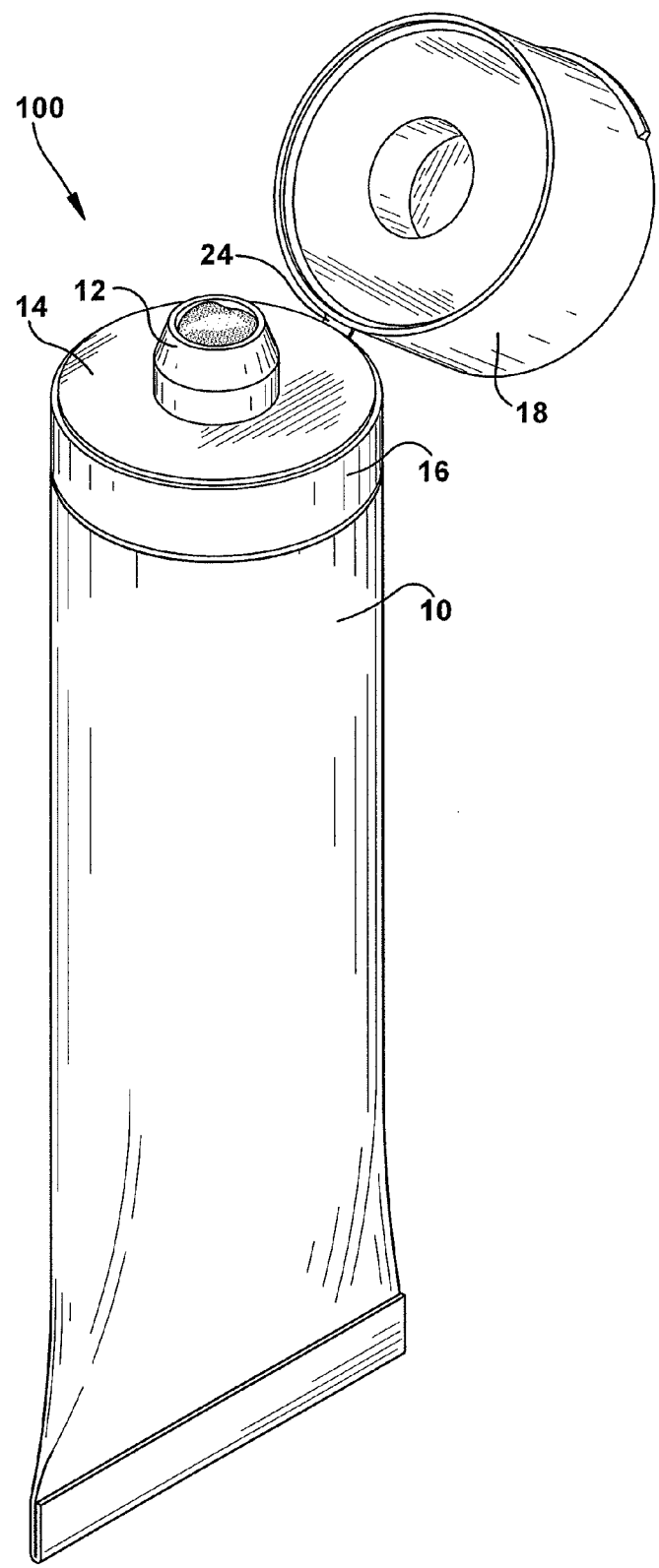
FIG. 3 is a perspective view of the combined toothpaste container cap dental floss dispenser of FIG. 1 with an open toothpaste cap.
Figure 4:
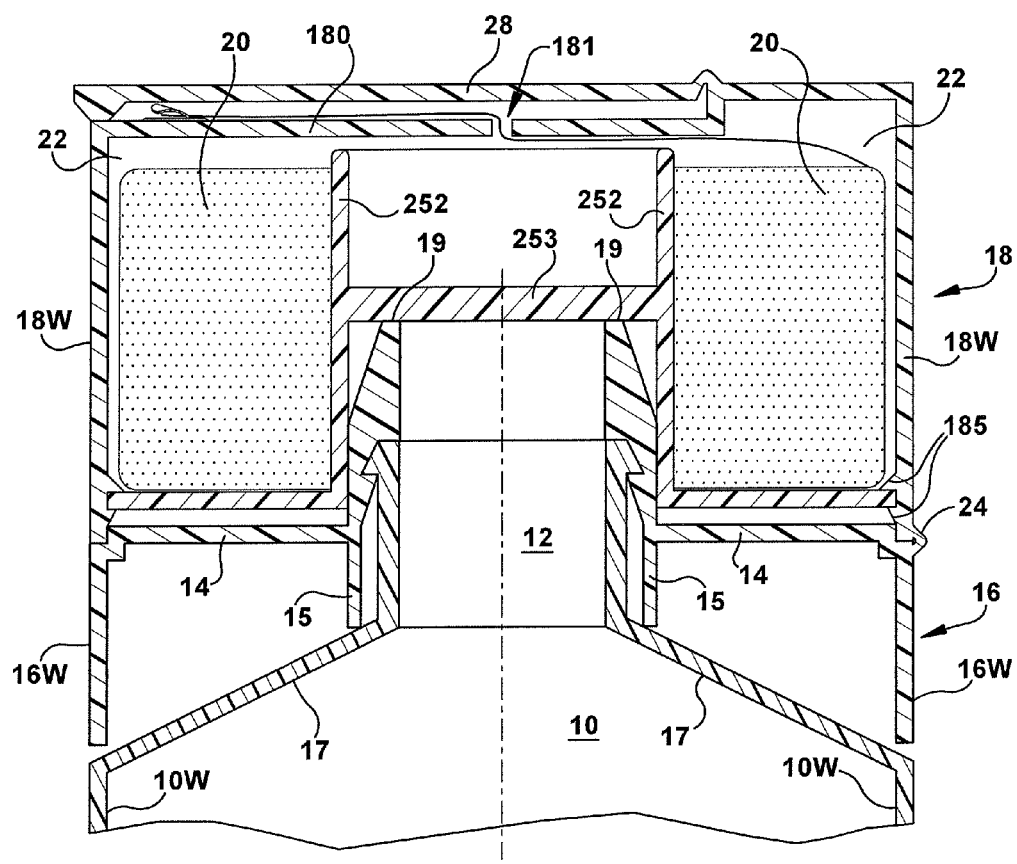
FIG. 4 is a cross-sectional view of the top (cap) portion of the combined toothpaste container cap dental floss dispenser of FIG. 1.

As illustrated in FIGS. 1-4 and particularly in FIG. 4, a toothpaste container 10 in the general form of a tube, has a generally cylindrical dispensing port 12, the dispensing port 12 connected to the tube 10 by a tapered flange 17 which extends from the dispensing port 12 to a generally cylindrical side wall 10W of the tube 10 and a tube end. The flange 17 may be formed integrally with the side wall 10W of the tube 10. The combined toothpaste container caps and dental floss dispensers 100 of the present disclosure are not limited to any particular configuration of a toothpaste containers 10 or any particular configuration of dispensing port 12 or flange 17 or other structure by which toothpaste is dispensed from the container.

Figure 5:
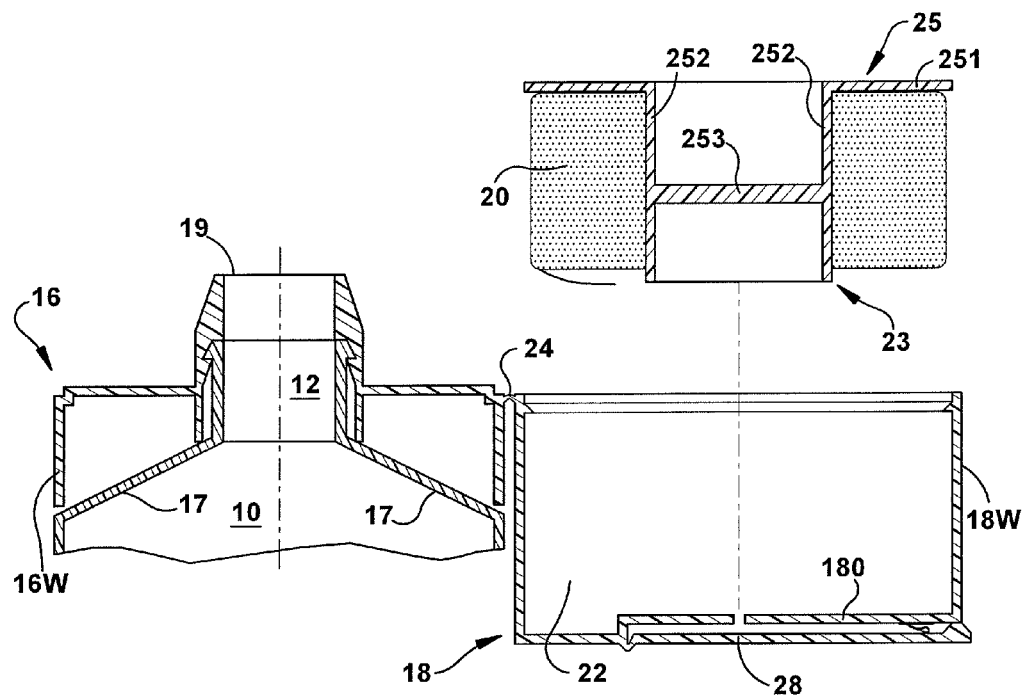
FIG. 5 is an assembly drawing of one embodiment of a combined toothpaste container and dental floss dispenser in combination with an end portion of a toothpaste container.
Figure 6:
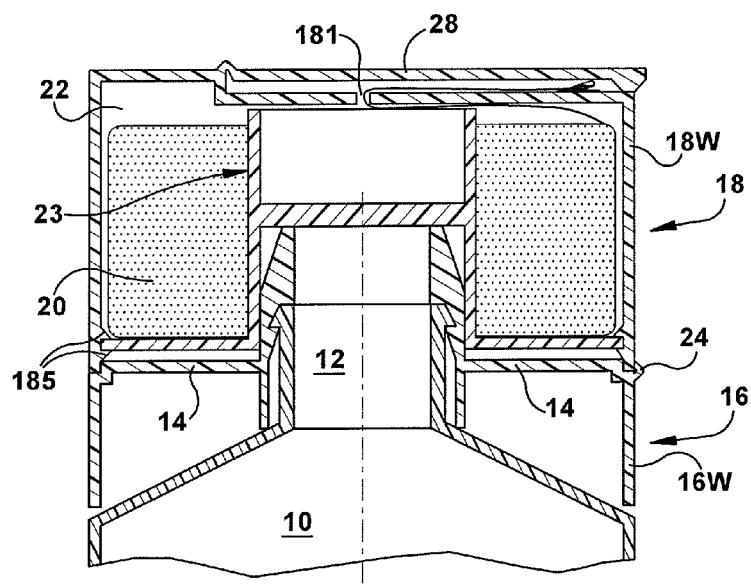
FIG. 6 is a cross-sectional view of the top (cap) portion of the combined toothpaste container cap dental floss dispenser of FIGS. 4 and 5.

As further shown in FIGS. 4-6, a first embodiment of a combined toothpaste container caps and dental floss dispenser 100 has the primary components of a cap body 16, a floss container body 18, and a floss cartridge 200. In this embodiment, the cap body 16 has internal structure 19 which is in the form of a passageway and configured to fit and engage with and generally align with the dispensing port 12 of the toothpaste container 10, whether by mating ring and groove engagement as shown or by helical thread engagement. The invention is not limited to any particular type of connection between the combined toothpaste container cap and dental floss dispenser 100 and the toothpaste container 10. The structure 19 of the cap body 16 is supported by a flange 14 which extends from the structure 19 to an outer wall 16W of the cap body 16. The outer wall 16W of the cap body 16 is configured to align with or fit over a portion of the side wall 10W of the tube 10, as shown in general alignment in FIGS. 4, 6 and 8. The outer wall 16W of the cap body 16 is not limited to any particular external configuration, and may or may not conform to an external configuration of a toothpaste container with which it is combined. Also, the internal structure of the cap body 16, such as structure 19 and flange 14, may be in any suitable form for engagement with a dispensing port of a container regardless of the external configuration of the container 10 or the combined container cap and dental floss dispenser 100. In the illustrated representative embodiment, a generally cylindrical container 10, in the general form of a tube, has generally cylindrical side walls and a circular flange from which a dispensing port 12 extends. Accordingly the outer wall 16W of the cap body 16 is also generally cylindrical and of the same or similar diameter as the side wall of the container 10. For example, the generally cylindrical outer wall 16W of the cap structure 16 is aligned or parallel with the generally cylindrical side wall 10W of the dispensing end of a tube type toothpaste container 10. When aligned with the container side wall 10W, terminal ends of the cap body outer wall 16W may abut or be proximate to the flange 17 of the container end. One or more depending flanges 15 may be formed to extend from the continuous flange 14 to or proximate to the tapered flange 17 of the container end. The dispensing port 12 of the container 10 may be circular and cylindrical, and the internal structure 19 of the cap body 16 accordingly also cylindrical to fit over or otherwise engage with the dispensing port 12. The internal cylindrical structure 19 of the cap body 16 also includes an opening through which the cylindrical dispensing port 12 of the tube 10 extends.

As further shown in FIGS. 4, 5 and 6, a floss container body 18 is attached to the cap body 16, for example by a hinge 24. The hinge 24 may be formed as a molded hinge integral with cap body 16 and floss container body 18. The floss container body 18 has a side wall structure 18W which generally fits or is aligned with the side wall 16W of the cap body 16, for example as mating cylinders, although other configurations are possible. The floss container body 18 is configured to engage with the cap body 16, and preferably to lockingly engage such as a snap fit either between the internal structures of the floss container body 18 and the cap body 16, or between the mating outer walls 18W of the floss container body 18 and the outer wall 16W of the cap body 16. Disengagement of the floss container body 18 from the cap body 16 exposes the tube dispensing port 12, as shown in FIG. 3.

The floss container body 18 has internal structure which defines a floss containment cavity 22 configured to hold a supply of dental floss 20. The dental floss 20 is preferable in a continuous strand, although the disclosure and related inventions contemplate multiple individual strands, segmented strands or connected but separable strands which is wound, packed or otherwise arranged within the floss containment cavity 22 as further described. A high density of floss can be loaded into the floss container body 18 in the floss containment cavity 22 and extracted or dispensed through an opening in the floss container body 18, such as opening 181 formed in a top wall 180 of the floss container body 18. Within the floss containment cavity 22 there may be provided a floss cartridge 25 which has a base 251 and a hub 23 formed by vertical walls 252 and a cross-member 253. The floss cartridge 25 is shown removed from the floss containment cavity 22 in FIG. 8. The hub 23 of the floss cartridge 25 is generally aligned with the cylindrical structure 19 of the cap body 16 and the tube dispensing port 12. And the cross-member 253 extends across the dispensing port 12 when in the closed position as shown in FIG. 6 to seal the container 10. Alternate embodiments may not have a cartridge or spool or other piece for the floss 20 in the floss containment cavity 22. The floss supply may be in spool-less form or packed form within the floss containment cavity 22.

The floss container body 18 is preferably attached to the cap body 16 by a flexible connection which can function as a hinge 24, such as a living hinge, whereby upon disengagement of the floss container body 18 from the cap body 16, the floss container body 18 can be opened relative to the cap body 16 about hinge 24, exposing the tube dispensing port 12 through the opening in the cap body 16 for dispensing of toothpaste from the container 10. The hinge 24 may be in any form, such as for example a strip of flexible plastic material which extends from a side wall of the floss container body 18 to the side wall of the cap body 16 and which is integrally formed therewith. However, a hinged connection or any permanent connection between the floss container body 18 and the cap body 16 is not required.

As further shown in FIGS. 4-6, the floss cartridge 25 is installed and engaged within the floss container body 18 with the base 251 extending substantially to the interior surface of walls 18W and the vertical walls 252 of the hub 23 extending proximate to the interior of the top wall 180 of the floss container body 18. The floss cartridge 25 is held in position within the floss container body 18 preferably by snap-fit engagement of the edges of base 251 within or between opposing chocks 185 on the interior side of walls 18W, or in a detent formed on the interior side of walls 18W, and by the contact of the cross-member 253 with the distal end of the structure 19 of the cap body 16. The floss 20 is threaded over the distal ends of the walls 252, which may be tapered or rounded as shown, and through the opening 181 in the top wall 180 of the floss container body 18. When the floss cartridge 25 is fully engaged within the floss container body 18, the floss F is completely encapsulated within the floss container body 18 and maintained therein in a sterile and dry environment for dispensing only through a small opening in the floss container body 18.

In the described arrangement, the supply of floss 20 is located at least partially around the dispensing port 12 of the tube 10, but can also be located generally distally of the dispensing port 12 of the tube 10. Access to the floss 20 is gained through the floss container body 18, for example through an opening in the floss container body 18, referred to herein as the "floss lead opening" 32, through which a lead end of the floss is threaded. In the embodiment shown in FIGS. 1 through 4, the floss lead opening is located on the distal end or top wall 181 of the floss container body 18. The floss lead opening 32 may be located anywhere in relation to the top wall 181 in accordance with this embodiment. A cover or access panel 28 can be provided to fit within the floss container body 18 to cover the floss lead opening 32, shown in FIG. 1. The cover or access panel 28 can be attached by a hinge 34 to the floss container body 18, as shown in FIG. 2, and also be configured to lockingly engage with the floss container body 18.

Alternatively, as shown in FIGS. 7-11, the floss lead opening 32 is located on the outer wall 18W of the floss container body 18. The cover or access panel 28 is hingedly attached to the floss container body 18 about a hinge, as shown in FIG. 8. A small opening or slot between the cover or access panel 28 and the floss container body 18 is configured to provide a gripping point whereby the cover or access panel 28 can be opened to expose the floss lead opening 32.

Figures 1, 2:
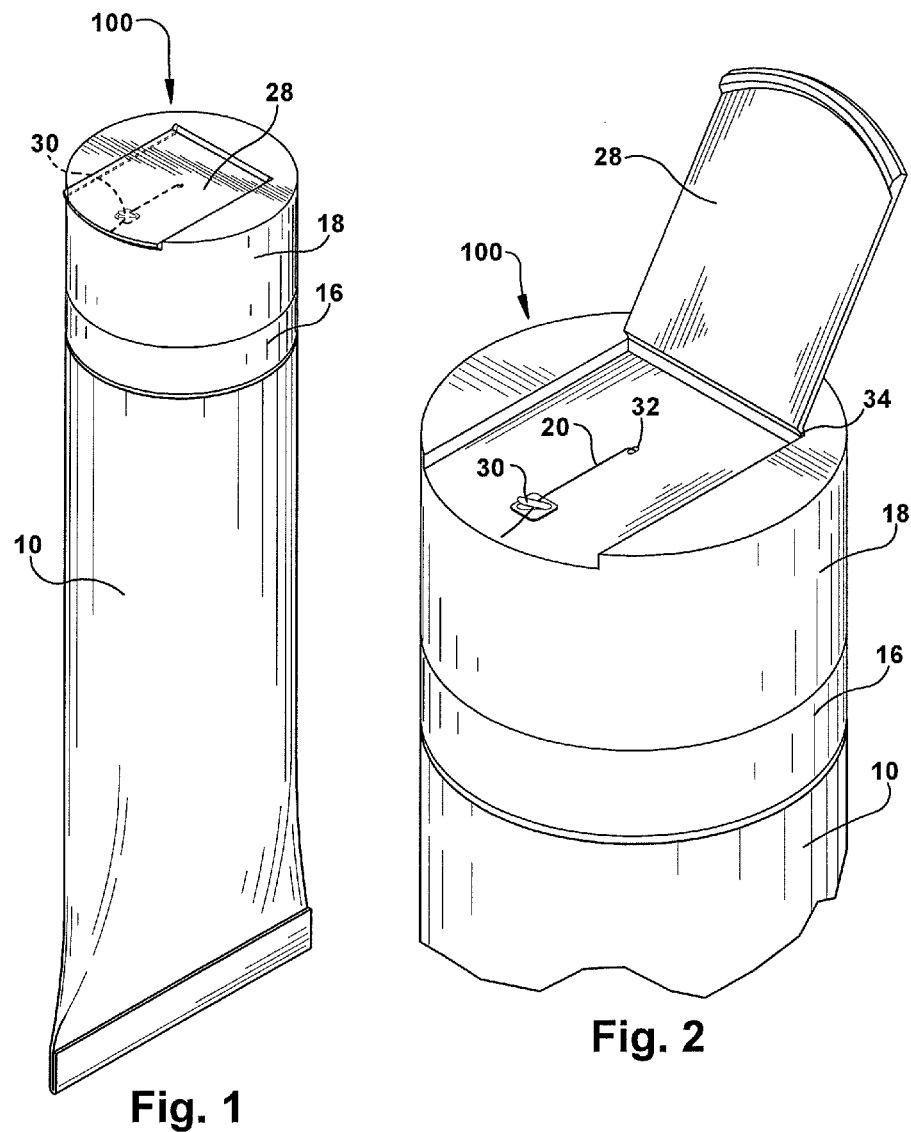
FIG. 1 is a perspective view of a combined toothpaste container cap dental floss dispenser of the present invention.
FIG. 2 is a perspective view of a top (cap) portion of the combined toothpaste container cap dental floss dispenser of FIG. 1 with a top floss access panel.

A cutter 30 can be incorporated into the floss container body 18, preferably closely proximate to the floss lead opening 32, as shown in FIGS. 2 and 8. The cutter 30 can be integrated into the structure of the floss container body 18, such as, for example, by formation of a cutting edge against which the floss is pulled to sever a piece. Alternatively, a separate cutting blade or device can be attached to the floss container body and oriented for cutting interface with the floss pulled through the lead opening. As mentioned above, the floss lead opening 32 can be located anywhere in the floss container body 18, whether through the outer side wall (FIG. 6) or through a distal end wall (FIG. 2) which extends over the floss containment cavity 22 and between the outer wall of the floss container body 18.

Figure 10:
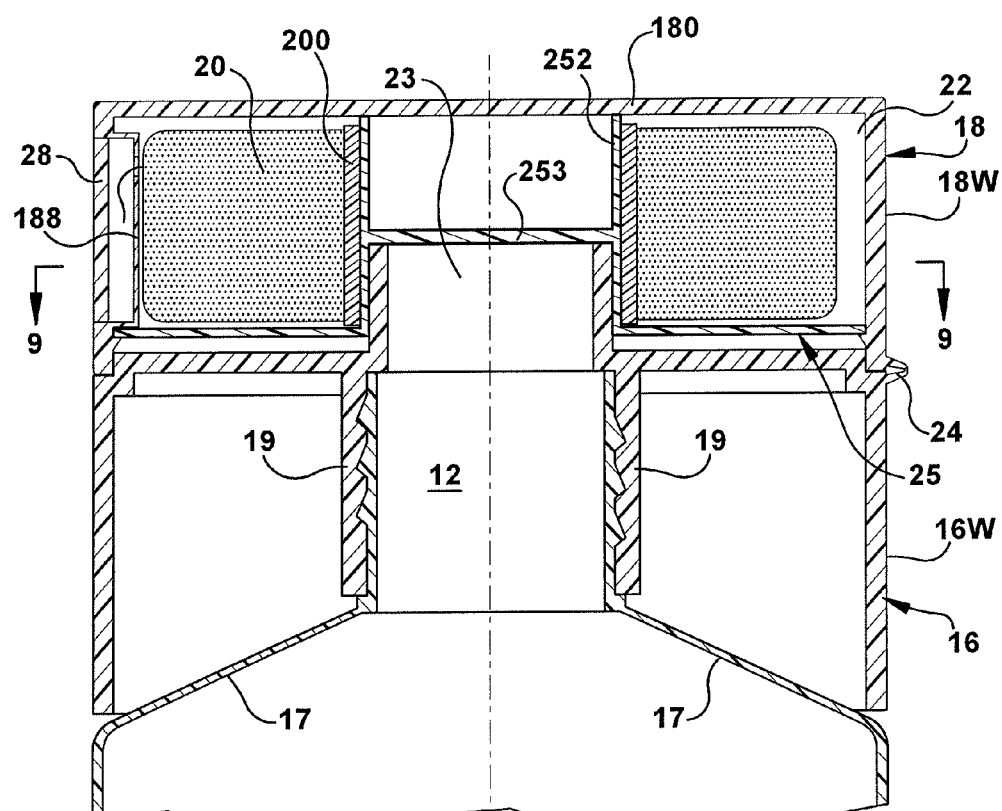
FIG. 10 is a cross-sectional view of the top (cap) portion of the combined toothpaste container cap dental floss dispenser of FIGS. 7-9.

FIG. 10 illustrates a representative interior structure of the combined toothpaste container cap and dental floss dispenser 100 of this embodiment. This embodiment also includes a cap body 16 and a floss container body 18 attached together by hinge 24. The cap body 16 is similarly configured with structure 19 which engages with a dispensing port, whether by threaded engagement or single or multiple opposing ring snap fit engagement as previously described with reference to FIG. 4. A floss cartridge 25 fits within the floss container body 18, and can be snap fit within chocks 185 and with distal ends of the vertical walls 252 proximate to or abutting against the top wall 180 of the floss container body 18. A floss spool 200, around which floss 20 is wound, is installed for rotation about the hub 23 of the cap body 16, with the floss 20 exiting the floss container body 18 through a side wall 188. By this arrangement, the floss cartridge 18 can be quickly and easily loaded with floss by installation of a floss spool 200 over hub 23. Snap-fit installation of the floss cartridge 18 thus loaded into the floss containment body 18 easily and quickly completes the assembly of the device.

The combined toothpaste container cap dental floss dispensers 100 of the disclosure provide novel closure and floss dispensing devices for use with existing toothpaste container closure, the ample supply of dental floss being easily accessible and length selectable, and without interference with operation or modification of the toothpaste container.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

What is claimed is:

1. A combined toothpaste container cap and dental floss dispenser adapted for connection to a generally cylindrical toothpaste tube having a dispensing port connected to the tube by a tapered flange which extends from the dispensing port to a side wall of the toothpaste tube at a tube end, the combined toothpaste container cap and dental floss dispenser comprising:

a cap body having a generally cylindrical structure which fits around and attaches to the dispensing port, the cylindrical structure having an opening which is aligned with the dispensing port of the toothpaste tube when the cap body is attached to the dispensing port of the toothpaste tube, and a cylindrical internal structure to fit over the dispensing port; the cap body further comprising a continuous flange which extends radially from the cylindrical structure to an outer cylindrical wall of the cap body located radially outward of the cylindrical structure;

a floss container body removably attached to the cap body, the floss container body having an internal cavity configured to receive a floss cartridge which is engaged with the internal cavity of the floss container body in a fixed and non-rotatable position, the floss cartridge comprised of a base configured to fit within the outer cylindrical wall of the cap body, a hub formed by a cylindrical wall which extends perpendicularly from the base, and a cross member perpendicular to and within the cylindrical wall of the hub, the floss cartridge holding a quantity of dental floss disposed about the hub and proximate to the base, the cylindrical internal structure configured to fit inside the hub when the floss container body is attached to the cap body; the base, hub and cross member of the floss cartridge forming a continuous and uninterrupted structure which occludes the opening of the cylindrical structure of the cap body when the floss container body is attached to the cap body;

an aperture located in a top wall of the floss container body through which the dental floss extends from the floss cartridge for access.

2. The combined toothpaste container cap and dental floss dispenser of claim 1, wherein the floss container body is lockingly engageable with the cap body.

3. The combined toothpaste container cap and dental floss dispenser of claim 1, wherein the floss container body is attached to the cap body by a flexible attachment.

4. The combined toothpaste container cap and dental floss dispenser of claim 1 further comprising a cover engaged with the floss container body and covering the floss lead opening.

5. The combined toothpaste container cap and dental floss dispenser of claim 1, further comprising a cutter for severing a portion of dental floss from the supply of dental floss.

6. The combined toothpaste container cap and dental floss dispenser of claim 1, wherein the access panel is located on a distal end of the floss container body.

7. The combined toothpaste container cap and dental floss dispenser of claim 1, wherein the cap body and floss container body are connected along a hinge.

8. The combined toothpaste container cap and dental floss dispenser of claim 1, wherein detachment of the floss container body from the cap body reveals the dispensing port.

* * * * *